United States Patent
Kao et al.

(10) Patent No.: US 6,383,762 B1
(45) Date of Patent: *May 7, 2002

(54) METHODS OF OBTAINING COMPOUNDS THAT INTERACT WITH A HUMAN SEROTONIN (5-HT$_2$) RECEPTOR

(75) Inventors: Hung-Teh Kao, Hackensack; Paul R. Hartig, Mahwah; Theresa Branchek, Teaneck, all of NJ (US)

(73) Assignee: Synaptic Pharmaceutical Corporation, Paramus, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/145,864

(22) Filed: Sep. 2, 1998

Related U.S. Application Data

(62) Division of application No. 08/613,044, filed on Mar. 8, 1996, now Pat. No. 5,885,785, which is a division of application No. 08/347,591, filed on Nov. 30, 1994, now Pat. No. 5,661,024, which is a continuation of application No. 08/232,325, filed on Apr. 25, 1994, now abandoned, which is a continuation of application No. 07/999,661, filed on Dec. 29, 1992, now abandoned, which is a continuation of application No. 07/635,402, filed on Dec. 31, 1990, now abandoned, which is a continuation of application No. 07/429,832, filed on Oct. 31, 1989, now abandoned.

(51) Int. Cl.$^7$ .................... G01N 33/566; C12N 5/16; C12N 15/12; C07K 14/705
(52) U.S. Cl. .................... 435/7.21; 435/69.1; 435/325; 530/350; 536/23.5
(58) Field of Search .................. 436/501; 435/69.1, 435/252.3, 6, 7, 7.2, 7.21, 7.1, 240.2, 325; 514/2; 530/350; 536/23.5

(56) References Cited

U.S. PATENT DOCUMENTS

| | | |
|---|---|---|
| 4,985,352 A | 1/1991 | Julius et al. |
| 5,155,218 A | 10/1992 | Weinshank et al. |
| 5,360,735 A | 11/1994 | Weinshank et al. |
| 5,472,866 A | 12/1995 | Gerald et al. |
| 5,476,782 A | 12/1995 | Weinshank et al. |
| 5,661,024 A | 8/1997 | Kao et al. .............. 435/240.2 |
| 5,885,785 A * | 3/1999 | Kao et al. .............. 435/7.21 |

FOREIGN PATENT DOCUMENTS

| | | |
|---|---|---|
| EP | 0565370 | 10/1993 |
| FR | 2696749 | 4/1994 |
| WO | 9506117 | 3/1995 |

OTHER PUBLICATIONS

Bowie et al, Science 247(1306–1310) 1990.*
Wells, Biochemistry 29(8509–8517) 1990.*
Ngo et al, The Protein Folding Problem and Tertiary Structure, pp 14–16, 1994.*
Kramer, R.A., et al., "Regulated expression of a Human Interferon Gene in Yeast: control by Phosphate concentration or temperature." *PNAS* (1984) 81: 366–370.
Cory, R.N., et al., "5–HT$_2$ Receptor–Stimulated Inositol Phosphate Formation in Rat Aortic Myocytes." *Euro. J. Pharm.* (1986) 131: 153–157.
Hoyer, D., et al., "Serotonin Receptors in the Human Brain. II. Characterization and Autoradiographic Localization of 5–HT$_{1C}$ and 5–HT$_2$ Recognition Sites." *Brain Research* (1986) 376: 97–107.
Lyon, R.A., et al., "$^3$H–DOB (4–Bromo–2, 5–Dimethoxyphenylisopropylamine) Labels Guanyl Nucleotide–Sensitive State of Cortical 5–HT$_2$ Receptors." *Mol. Pharm.* (1986) 31: 194–199.
Cory, R.N., et al., "The 5–Hydroxytryptamine (5–HT$_2$) Receptor Stimulates Inositol Phosphate Formation in Intact and Broken WRK1 Cells: Determination of Occupancy–Response Relationships for 5–HT Agonists." *J. Pharm. Exp. Ther.* (1987) 241(1): 258–267.
Shenker, A., et al., "Pharmacological Characterization of Two 5–Hydroxytryptamine Receptors Coupled to Adenylate Cyclase in Guinea Pig Hippocampal Membranes." *Mol. Pharm.* (1987) 31(4): 357–367.
Lubbert, H., et al., "cDNA Cloning of a Serotonin 5–HT$_{1C}$ Receptor by Electrophysiological Assays of mRNA–Injected Xenopus Oocyte." *Proc. Nat'l. Aca. Sci.* (1987) 84: 4332–4336.
Kobilka, B.K., et al., "An Intronless Gene Encoding a Potential Member of the Family of Receptors Coupled to Guanine Nucleotide Regulatory Proteins." *Nature* (1987) 329: 75–79.
Marzoni, G., et al., "6–Methylergoline–8–Carboxylic Acid Esters as Serotonin Antagonists: N$^1$–Substituted Effects on 5HT$_2$ Receptor Affinity." *J. Med. Chem.* (1987) 30(10): 1823–1826.
Kaufman, R.J., "High Level Production of Proteins in Mammalian Cells." *Genetic Engineering* (1987) 9: 155–198.
Stevens, C.F., "Channel Families in the Brain." *Nature* (1987) 328: 198–199.

(List continued on next page.)

Primary Examiner—Elizabeth Kemmerer
Assistant Examiner—Michael Brannock
(74) Attorney, Agent, or Firm—John P. White; Cooper & Dunham LLP

(57) ABSTRACT

The present invention provides a method of obtaining a composition which comprises determining whether a chemical compound binds to a human 5-HT$_2$ receptor expressed on the surface of a mammalian cell transfected with a vector adapted for expressing the receptor in the cell, and if the compound binds to the receptor, admixing the compound with a carrier. The present invention further provides a method of obtaining a composition which comprises determining whether a chemical compound binds to and activates or binds to and inhibits activation of a human 5-HT$_2$ receptor expressed on the surface of a mammalian cell, wherein the human 5-HT$_2$ receptor is expressed on the surface of a mammalian cell transfected with a vector adapted for expressing the receptor in the cell, and if the compound binds to and activates or binds to and inhibits activation of the receptor, admixing the compound with a carrier.

5 Claims, 10 Drawing Sheets

OTHER PUBLICATIONS

Fargin, A., et al., "The Genomic Clone G–21 which Resembles a β–Adrenergic Receptor Sequence Encodes the 5–HT$_{1A}$ Receptor." *Nature* (1988) 335: 358–360.

Harris, T.J., "Expression of Eukaryotic genes in *E. Coli.*" *Genetic Engineering* (1988) 4: 127–141.

Julius, D., et al., "Molecular Characterization of a Functional cDNA Encoding the Serotonin 1c Receptor." *Science* (1988) 241: 558–564.

Pritchett, D.B., et al., "Structure and Functional Expression of Cloned Rat Serotonin 5HT–2 Receptor." *EMBO J.* (1988) 7: 4135–4140.

Pierce, P., et al., Evidence for Distinct 5–Hydroxytryptamine$_2$ Binding Site Subtypes in Cortical Membrane Preparations. *J. Neurochem.* (1989) 52: 656–658.

Amstein, R., et al., "Platelet Deactivation by 5HT–2–Receptor Blockade Parallels the Antihypertensive Response to Ketanserin." *J. Hypertens.* (1989) 7(4): 255–260.

Wright, C.E., et al., "5–Carboxamidotryptamine Elicits 5–HT$_2$ and 5–HT$_3$ Receptor–Mediated Cardiovascular Responses in the Conscious Rabbit: Evidence for 5–HT Release from Platelets." *Cardiovasc. Pharm.* (1989) 13(4): 557–564.

Strader, C.D., et al., "Structural basis of β–Adrenergic Receptor function." *FASEB J.* (1989) 3: 1825–1832.

Schmidt, A.W., et al., "5–Hydroxytryptamine Receptor Families." *FASEB J.* (1989) 3: 2242–2250.

Cohen, M.L., et al., "Lack of a Difference Between Ketanserin and Ritanserin in Central vs. Peripheral Serotonin Receptor Antagonism." *Life Sci.* (1989) 45(13): 1185–1189.

Cohen, M.L., et al., "Effect of LY53857, A Selective 5HT$_2$ Receptor Antagonist, on 5HT–Induced Increases in Cutaneous Vascular Permeability in Rats." *Life Sci.* (1989) 44(14): 957–961.

Baez, M., et al., "Pharmacological and Molecular Evidence that the Contractile Response to Serotonin in Rat Stomach Fundus Is Not Mediated by Activation of the 5–Hydroxytryptamine$_{1C}$ Receptor." *Mol. Pharm.* (1990) 38(1): 31–37.

Branchek, T., et al., "[$^3$H]–DOB(4–Bromo–2, 5–Dimethoxyphenylisopropylamine) and [$^3$H] Ketanserin Label Two Affinity States of the Cloned Human 5–Hydroxytryptamine$_2$ Receptor." *Mol. Pharm.* (1990) 38: 604–609.

Hartig, P., et al., "The Molecular Biology of Serotonin Receptors." *Neuropsychopharmacology* (1990) 3(5/6): 335–347.

Julius, D., et al., "The 5HT2 Receptor Defines a Family of Structurally Distinct but Functionally Conserved Serotonin Receptors." *Proc. Natl. Acad. Sci.* (1990) 87: 928–932.

Saltzman, A.G., et al., "Cloning of the Human Serotonin 5–HT2 and 5HT1C Receptor Subtypes." *Biochem. Biophys. Res. Comm.* (1991) 181(3): 1469–1478.

Kao, H.T., et al., "Site–Directed Mutagenesis of a Single Residue Changes the Binding Properties of the Serotonin 5–HT$_2$ Receptor from a Human to a Rat Pharmacology." *FEBS Letters* (1992) 307(3): 324–328.

Mita et al., Evidence for the presence of D2 and 5–HT2 receptors in the human prefrontal cortex. Jap. J. Pharmacol. 32: 1027–1032, 1982.

* cited by examiner

FIGURE 2

```
Met Asp Ile Leu Cys Glu Glu Asn Thr Ser
ATG GAT ATT CTT TGT GAA GAA AAT ACT TCT
                10                    20                    30

Leu Ser Ser Thr Thr Asn Ser Leu Met Gln
TTG AGC TCA ACT ACG AAC TCC CTA ATG CAA
                40                    50                    60

Leu Asn Asp Asp Thr Arg Leu Tyr Ser Asn
TTA AAT GAT GAC ACC AGG CTC TAC AGT AAT
                70                    80                    90

Asp Phe Asn Ser Gly Glu Ala Asn Thr Ser
GAC TTT AAC TCC GGA GAA GCT AAC ACT TCT
               100                   110                   120

Asp Ala Phe Asn Trp Thr Val Asp Ser Glu
GAT GCA TTT AAC TGG ACA GTC GAC TCT GAA
               130                   140                   150

Asn Arg Thr Asn Leu Ser Cys Glu Gly Cys
AAT CGA ACC AAC CTT TCC TGT GAA GGG TGC
               160                   170                   180
```

FIGURE 2 (cont.)

```
  Leu   Ser   Pro   Ser   Cys   Leu   Ser   Leu   Leu   His
  C T C T C A C C G T C G T G T C T C T C C T T A C T T C A T
              190                 200                 210

Leu   Gln   Glu   Lys   Asn   Trp   Ser   Ala   Leu   Leu
  C T C C A G G A A A A A A A C T G G T C T G C T T T A C T G
              220                 230                 240

Thr   Ala   Val   Val   Ile   Ile   Leu   Thr   Ile   Ala
  A C A G C C G T A G T G A T T A T T C T A A C T A T T G C T
              250                 260                 270

Gly   Asn   Ile   Leu   Val   Ile   Met   Ala   Val   Ser
  G G A A A C A T A C T C G T C A T C A T G G C A G T G T C C
              280                 290                 300

Leu   Glu   Lys   Lys   Leu   Gln   Asn   Ala   Thr   Asn
  C T A G A G A A A A A G C T G C A G A A T G C C A C C A A C
              310                 320                 330

Tyr   Phe   Leu   Met   Ser   Leu   Ala   Ile   Ala   Asp
  T A T T T C C T G A T G T C A C T T G C C A T A G C T G A T
              340                 350                 360

Met   Leu   Leu   Gly   Phe   Leu   Val   Met   Pro   Val
  A T G C T G C T G G G T T T C C T T G T C A T G C C C G T G
              370                 380                 390

Ser   Met   Leu   Thr   Ile   Leu   Tyr   Gly   Tyr   Arg
  T C C A T G T T A A C C A T C C T G T A T G G G T A C C G G
              400                 410                 420
```

FIGURE 2 (cont.)

```
Trp Pro Leu Pro Ser Lys Leu Cys Ala Val
T G G C C T C T G C C G A G C A A G C T T T G T G C A G T C
         430             440             450

Trp Ile Tyr Leu Asp Val Leu Phe Ser Thr
T G G A T T T A C C T G G A C G T G C T C T T C T C C A C G
         460             470             480

Ala Ser Ile Met His Leu Cys Ala Ile Ser
G C C T C C A T C A T G C A C C T C T G C G C C A T C T C G
         490             500             510

Leu Asp Arg Tyr Val Ala Ile Gln Asn Pro
C T G G A C C G C T A C G T C G C C A T C C A G A A T C C C
         520             530             540

Ile His His Ser Arg Phe Asn Ser Arg Thr
A T C C A C C A C A G C C G C T T C A A C T C C A G A A C T
         550             560             570

Lys Ala Phe Leu Lys Ile Ile Ala Val Trp
A A G G C A T T T C T G A A A A T C A T T G C T G T T T G G
         580             590             600

Thr Ile Ser Val Gly Ile Ser Met Pro Ile
A C C A T A T C A G T A G G T A T A T C C A T G C C A A T A
         610             620             630

Pro Val Phe Gly Leu Gln Asp Asp Ser Lys
C C A G T C T T T G G G C T A C A G G A C G A T T C G A A G
         640             650             660
```

FIGURE 2 (cont.)

```
Val  Phe  Lys  Glu  Gly  Ser  Cys  Leu  Leu  Ala
G T C T T T A A G G A G G G G A G T T G C T T A C T T G C C
        670           680           690

Asp  Asp  Asn  Phe  Val  Leu  Ile  Gly  Ser  Phe
G A T G A T A A C T T T G T C C T G A T C G G C T C T T T T
        700           710           720

Val  Ser  Phe  Phe  Ile  Pro  Leu  Thr  Ile  Met
G T G T C A T T T T T C A T T C C C T T A A C C A T C A T G
        730           740           750

Val  Ile  Thr  Tyr  Phe  Leu  Thr  Ile  Lys  Ser
G T G A T C A C C T A C T T T C T A A C T A T C A A G T C A
        760           770           780

Leu  Gln  Lys  Glu  Ala  Thr  Leu  Cys  Val  Ser
C T C C A G A A A G A A G C T A C T T T G T G T G T A A G T
        790           800           810

Asp  Leu  Gly  Thr  Arg  Ala  Lys  Leu  Ala  Ser
G A T C T T G G C A C A C G G C C A A A T T A G C T T C T
        820           830           840

Phe  Ser  Phe  Leu  Pro  Gln  Ser  Ser  Leu  Ser
T T C A G C T T C C T C C C T C A G A G T T C T T T G T C T
        850           860           870

Ser  Glu  Lys  Leu  Phe  Gln  Arg  Ser  Ile  His
T C A G A A A A G C T C T T C C A G C G G T C G A T C C A T
        880           890           900
```

FIGURE 2 (cont.)

```
Arg Glu Pro Gly Ser Tyr Thr Gly Arg Arg
A G G G A G C C A G G G T C C T A C A C A G G C A G G A G G
        910                 920                 930

Thr Met Gln Ser Ile Ser Asn Glu Gln Lys
A C T A T G C A G T C C A T C A G C A A T G A G C A A A A G
        940                 950                 960

Ala Cys Lys Val Leu Gly Ile Val Phe Phe
G C A T G C A A G G T G C T G G G C A T C G T C T T C T T C
        970                 980                 990

Leu Phe Val Val Met Trp Cys Pro Phe Phe
C T G T T T G T G G T G A T G T G G T G C C C T T T C T T C
       1000                1010                1020

Ile Thr Asn Ile Met Ala Val Ile Cys Lys
A T C A C A A A C A T C A T G G C C G T C A T C T G C A A A
       1030                1040                1050

Glu Ser Cys Asn Glu Asp Val Ile Gly Ala
G A G T C C T G C A A T G A G G A T G T C A T T G G G C C
       1060                1070                1080

Leu Leu Asn Val Phe Val Trp Ile Gly Tyr
C T G C T C A A T G T G T T T G T T T G G A T C G G T T A T
       1090                1100                1110

Leu Ser Ser Ala Val Asn Pro Leu Val Tyr
C T C T C T T C A G C A G T C A A C C C A C T A G T C T A C
       1120                1130                1140
```

FIGURE 2 (cont.)

```
Thr Leu Phe Asn Lys Thr Tyr Arg Ser Ala
A C A C T G T T C A A C A A G A C C T A T A G G T C A G C C
        1150              1160              1170

Phe Ser Arg Tyr Ile Gln Cys Gln Tyr Lys
T T T T C A C G G T A T A T T C A G T G T C A G T A C A A G
        1180              1190              1200

Glu Asn Lys Lys Pro Leu Gln Leu Ile Leu
G A A A A C A A A A A A C C A T T G C A G T T A A T T T T A
        1210              1220              1230

Val Asn Thr Ile Pro Ala Leu Ala Tyr Lys
G T G A A C A C A A T A C C G G C T T T G G C C T A C A A G
        1240              1250              1260

Ser Ser Gln Leu Gln Met Gly Gln Lys Lys
T C T A G C C A A C T T C A A A T G G G A C A A A A A A A G
        1270              1280              1290

Asn Ser Lys Gln Asp Ala Lys Thr Thr Asp
A A T T C A A A G C A A G A T G C C A A G A C A A C A G A T
        1300              1310              1320

Asn Asp Cys Ser Met Val Ala Leu Gly Lys
A A T G A C T G C T C A A T G G T T G C T C T A G G A A A G
        1330              1340              1350

Gln His Ser Glu Glu Ala Ser Lys Asp Asn
C A G C A T T C T G A A G A G G C T T C T A A A G A C A A T
        1360              1370              1380
```

FIGURE 2 (cont.)

```
Ser Asp Gly Val Asn Glu Lys Val Ser Cys
AGCGACGGAGTGAATGAAAAGGTGAGCTGT
         1390          1400          1410

Val *** *** Ala Ser Cys Arg Gly Asn Cys
GTGTGATAGGCTAGTTGCCGTGGCAACTGT
         1420          1430          1440

GGAAGGCACACTGAGCAAGTTTCACCTAT
         1450          1460          1470

CTGGTTTTTTTTG
         1480
```

METHODS OF OBTAINING COMPOUNDS THAT INTERACT WITH A HUMAN SEROTONIN (5-HT₂) RECEPTOR

This application is a divisional of U.S. Ser. No. 08/613,044, filed Mar. 8, 1996, U.S. Pat. No. 5,885,785 now allowed, which is a divisional of U.S. Ser. No. 08/347,591, filed Nov. 30, 1994, now U.S. Pat. No. 5,661,024, issued Aug. 26, 1997, which was a continuation of U.S. Ser. No. 08/232,325, filed Apr. 25, 1994, now abandoned, which was a continuation of U.S. Ser. No. 07/999,661, filed Dec. 29, 1992, now abandoned, which was a continuation of U.S. Ser. No. 07/635,402, filed Dec. 31, 1990, now abandoned, which was a continuation of U.S. Ser. No. 07/429,832, filed Oct. 31, 1989, now abandoned, the contents of which are hereby incorporated by reference.

BACKGROUND OF THE INVENTION

Throughout this application various publications are referenced by full citations within parentheses. The disclosures of these publications in their entireties are hereby incorporated by reference in this application in order to more fully described the state of the art to which this invention pertains.

Pharmacological studies, and more recently gene cloning, have established that multiple receptor subtypes exist for most, if not all, neurotransmitters. The existence of multiple receptor subtypes provides one mechanism by which a single neurotransmitter can elicit distinct cellular responses.

The variation in cellular response can be achieved by the association of individual receptor subtypes with different G proteins and different signalling systems. Further flexibility is provided by the ability of distinct receptors for the same ligand to activate or inhibit the same second messenger system.

Individual receptor subtypes reveal characteristic differences in their abilities to bind a number of ligands, but the structural basis for the distinct ligand-binding properties is not known. Physiologists and pharmacologists have attempted to specify particular biological functions or anatomical locations for some receptor subtypes, but this has met with limited success. Similarly, the biochemical mechanisms by which these receptors transduce signals across the cell surface have been difficult to ascertain without having well-defined cell populations which express exclusively one receptor subtype.

Receptors for serotonin (5-hydroxytryptamine) are termed serotonin or 5-HT receptors. The 5-HT₂ receptor belongs to the family of rhodopsin-like signal transducers which are distinguished by their seven-transmembrane configuration and their functional linkage to G-proteins. While all the receptors of the serotonin type are recognized by serotonin, they are pharmacologically distinct and are encoded by separate genes. These receptors, known as subtypes, are generally coupled to different second messenger pathways that are linked through guanine-nucleotide regulatory (G) proteins. Among the serotonin receptors, $5\text{-HT1}_A$, $5\text{-HT1}_B$, and $5\text{-HT1}_D$ receptors inhibit adenylate cyclase, and $5\text{-HT1}_C$ and $5\text{-HT}_2$ receptors activate phospholipase C pathways, stimulating breakdown of polyphosphoinositides.

Radioligand filtration binding techniques have been employed to characterize the serotonin receptor family (Schmidt and Peroutka, FASEB J. 3:2242 (1989)). Using these methods, at least two classes of G-protein coupled serotonin receptors have been described, $5\text{-HT}_1$, and $5\text{-HT}_2$. These differ in their selectivity for drugs. $5\text{-HT}_1$ receptors display high (nanomolar) affinity for serotonin and can be labeled with [³H] 5-HT. $5\text{-HT}_2$ receptors display low affinity for serotonin but have high (nanomolar) affinity for antagonists such as Ketanserin, Mesulergine, Metergoline and d-LSD. Genes for the $5\text{-HT}_{1A}$ receptor (Fargin, et al., Nature 335:358–360 (1988); Kobilka, et al., Nature 329:75–79 (1987)) and the $5\text{-HT}_{1C}$ receptor (Julius, et al., Science 241:588–564 (1988)) have been isolated.

Applicants have cloned a human $5\text{-HT}_2$ receptor, clone 6B, which has been transfected into a heterologous expression system, producing a membrane protein with binding properties consistent with its preliminary characterization based on amino acid homology as the $5\text{-HT}_2$ receptor subtype. The results from binding studies are consistent with the projected subtype based on amino acid sequence homology.

The receptor encoded by clone 6B shares numerous sequence and structural properties with the family of receptor molecules that has been predicted to span the lipid bilayer seven times. This family includes rhodopsin and related opsins (Nathans, J. and Hogness, D. S., Cell 34:807 (1983)), the α and β adrenergic receptors (Dohlman, H. G., et al., Biochemistry 26:2657 (1987)), the muscarinic cholinergic receptors (Bonner, T. I., et al., Science 237:527 (1987)), the substance K neuropeptide receptor, (Masu, Y., et al., Nature 329:836 (1987)), the yeast mating factor receptors, (Burkholder, A. C. and Hartwell, L. H., Nucl. Acids Res. 13:8463 (1985); Hagan, D. C., et al., Proc. Natl. Acad. Sci. USA 83:1418 (1986)); Nakayama, N. et al., EMBO J. 4:2643 (1985)), the serotonin receptor, and the oncogene c-mas, (Young, et al., Cell 45:711 (1986)). Each of these receptors is thought to transduce extracellular signals by interaction with guanine nucleotide-binding (G) proteins (Dohlman, H. G., et al., Biochemistry 26:2657 (1987); Dohlman, H. G., et al., Biochemistry 27:1813 (1988); O'Dowd, B. F., et al., Ann. Rev. Neurosci., in press).

Membranes of cells transfected with clone 6B bind both ³H-Ketanserin and ³H-DOB, demonstrating that the reported "hallucinogen receptor" must be an affinity state of the $5\text{-HT}_2$ receptor rather than a distinct receptor subtype. Thus, the argument of Titeler (Lyon, et al. Mol. Pharm. 31:194–199 (1987) for multiple affinity states of the $5\text{-HT}_2$ receptor is supported and that of Peroutka (Pierce, P. A., and S. J. Peroutka J. Neurochem. 52: 656–658 (1989)) for multiple $5\text{-HT}_2$ receptor subtypes is not. This observation provides the opportunity to use the transfected human $5\text{-HT}_2$ receptor as a tool for the development of drugs which induce or which interfere with hallucinogenesis, caused either by disease processes or by drugs of abuse.

Strader, Sigal and Dixon recently published a model for the neurotransmitter binding site of G protein-coupled receptors (FASEB J. 3: 1825–1832 (1989)). According to this model, adrenergic receptors contain two serine residues in transmembrane segment V (TM5) which hydrogen bond to the catechol ring hydroxyl groups of adrenergic agonists. Serotonergic receptors, which must bind agonist ligands containing a single ring hydroxyl group, are distinguished by a the presence of a single serine residue in this region of TM5. The rat serotonin $5\text{-HT}_2$ receptor sequence (Pritchett, et al., EMBO J. 7: 4135–4140 (1988)) shows a single serine residue in this region of TM5, as expected. Surprisingly, the human $5\text{-HT}_2$ receptor sequence shown in FIG. 2 violates this model by exhibiting two serine residues in this region, as would be expected for an adrenergic receptor. This raises the interesting possibility that the human $5\text{-HT}_2$ receptor may have evolved the possibility of interacting with epinephrine, norepinephrine and adrenergic antagonists, in addition to its known interactions with serotonergic drugs. This possible acquisition by the human 5-HT$_2$ receptor of a neurotransmitter cross-reactivity may have functional consequences in the normal or diseased human brain. We hypothesize that the human 5-HT$_2$ receptor may have evolved the capacity to interact with two separate neurotransmitter systems, the serotonergic and adrenergic systems. Since both systems are widely distributed in the brain and both may act in a neuromodulatory fashion to activate receptors far from the neurotransmitter release site, it is conceivable that the human 5-HT$_2$ receptor may be activated by a wide array of both serotonergic and adrenergic nerve terminals, In that case, classical adrenergic and serotonergic brain or peripheral nervous system functions may be mediated in part by this single receptor site. Thus, it may be possible to modulate serotonergic functions by administration of adrenergic drugs and to modulate adrenergic functions by administration of serotonergic drugs. These possibilities are currently under investigation in a variety of adrenergic and serotonergic binding, second messenger and physiological response assays.

Another interesting feature of the human 5-HT$_2$ receptor is the presence of a leucine zipper motif in transmembrane segment I (FIG. 3). This motif, consisting of four or more leucine residues repeated every seventh amino acid residue of an alpha-helix, has been implicated as the site of protein-protein interactions in dimerizing, or multisubunit proteins (McCormack et al. Nature 340: 103 (1989)). The presence of this motif in the human 5-HT$_2$ receptor suggests that this receptor may dimerize in the membrane or may interact with other unidentified proteins (or with G proteins) via the leucine zipper of transmembrane segment I. This may have significant implications for the function of the human 5-HT$_2$ receptor. In addition, it may be possible to design drugs which interfere with the leucine zipper region of the 5-HT$_2$ receptor, thus modulating the functional activity of this serotonergic response system.

SUMMARY OF THE INVENTION

The present invention provides an isolated nucleic acid molecule encoding a human 5-HT$_2$ receptor.

This invention also provides an isolated protein which is a human 5-HT$_2$ receptor.

The invention also provides vectors comprising DNA molecules encoding a human 5-HT$_2$ receptor, for example a plasmid comprising the DNA encoding the 5-HT$_2$ receptor, designated clone 6B.

Additionally, the present invention provides vectors adapted for expression in bacterial, yeast, or mammalian cells which comprise a DNA molecule encoding the 5-HT$_2$ receptor and the regulatory elements necessary for expression of the DNA in the cell.

The present invention further provides the transfected Ltk$^-$ cell designated L-NGC-5HT$_2$ and deposited under ATCC Accession No. CRL 10287.

In addition, the invention provides a DNA probe useful for detecting nucleic acid encoding the 5-HT$_2$ receptor comprising a nucleic acid molecule of at least about 15 nucleotides having a sequence complementary to a sequence included within the sequence shown in FIG. 2.

This invention also provides a method for determining whether a ligand which is not known to be capable of binding to the 5-HT$_2$ receptor can bind to the 5-HT$_2$ receptor.

This invention also concerns an antibody directed to the human 5-HT$_2$ receptor.

This invention additionally concerns a monoclonal antibody directed to an epitope of the 5-HT$_2$ receptor present on the surface of a cell and having an amino acid sequence included within the amino acid sequence shown in FIG. 2.

This invention concerns a method for detecting the presence of 5-HT$_2$ receptor on the surface of a cell.

This invention also concerns a method of screening drugs to identify drugs which specifically interact with, and bind to, the 5-HT$_2$ receptor.

The bold region represents the human 5-HT$_2$ coding sequence. Restriction sites are indicated.

FIG. 2. Nucleotide Sequence SEQ ID NO:1 and Deduced Amino Acid Sequence SEQ ID NO:2 of the Human 5-HT$_2$ Receptor.

Numbers indicate nucleotide position. DNA sequence of cDNA clone 6B was determined by the chain termination method of Sanger, et al., on denatured double-stranded plasmid templates (Chen and Seeburg, DNA 4:165,1985) using Sequenase. Deduced amino acid sequence by translation of a long open reading frame is shown.

Figure 1:
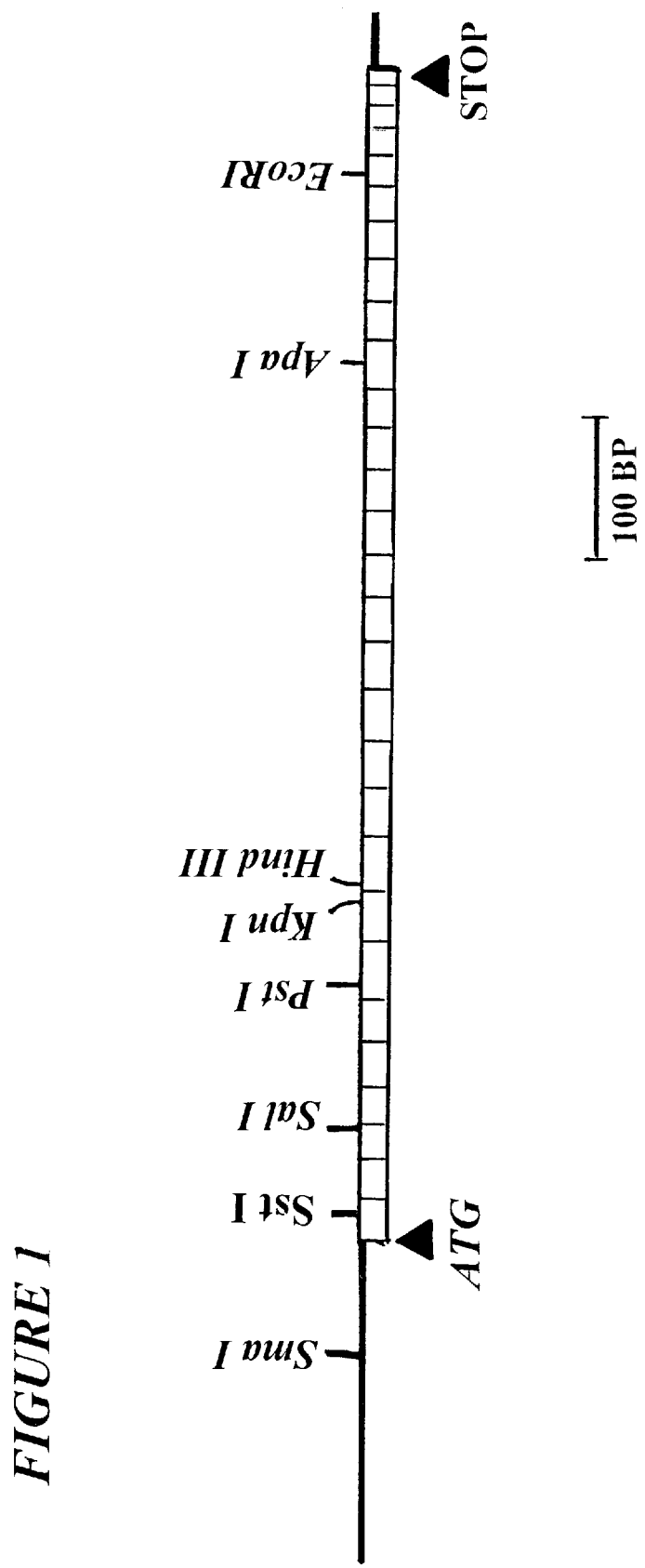
FIG. 1. Restriction Map of Clone.
Figure 3:
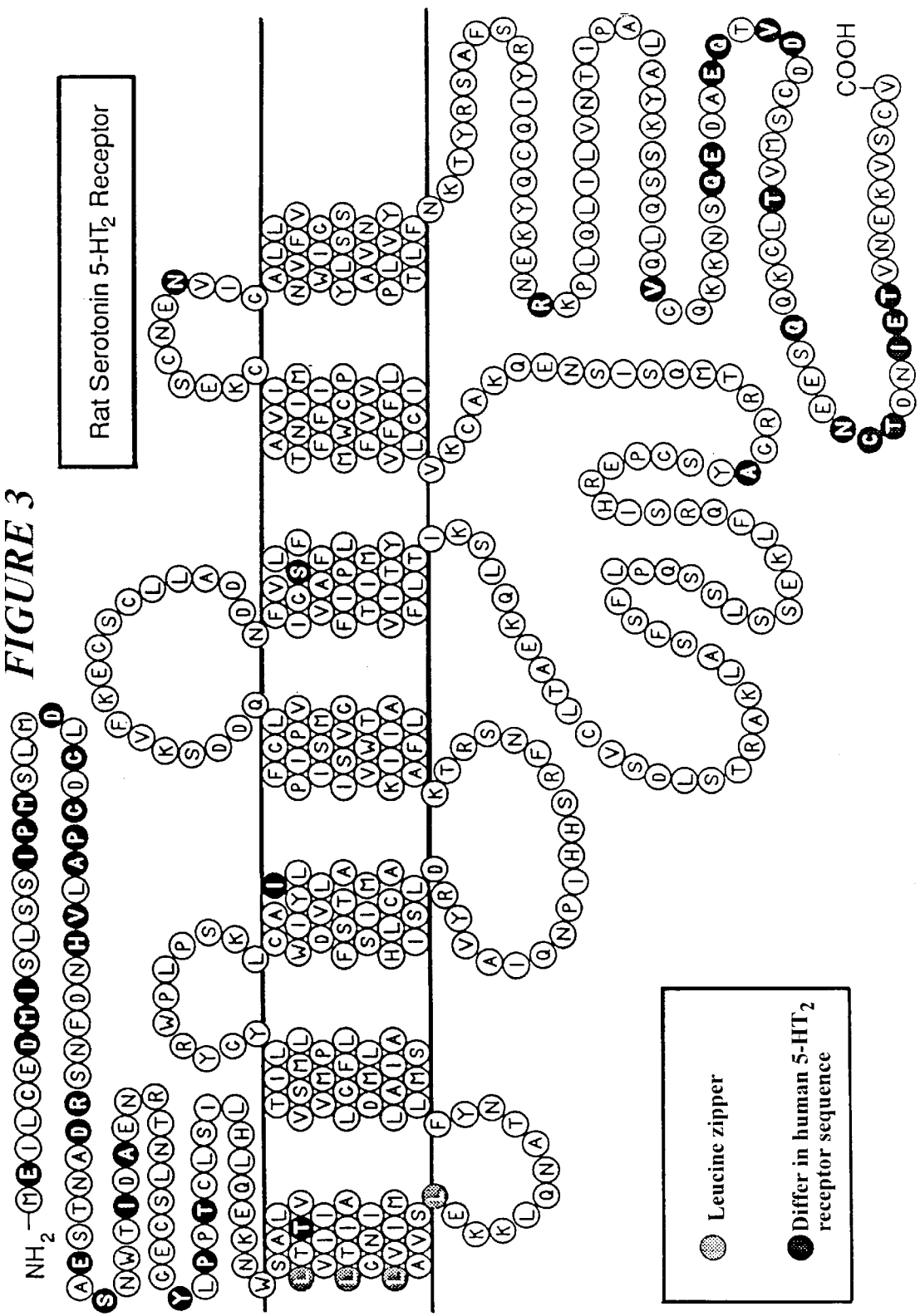

FIG. 3. Comparison of the Sequence Between the Rat and Human 5-HT$_2$ Receptors SEQ ID NO:4.

Amino acid sequences (single letter code) are pictured as a protein with the putative transmembrane domains traversing the membrane seven times. Differences are indicated as filled in circles.

Figure 4:
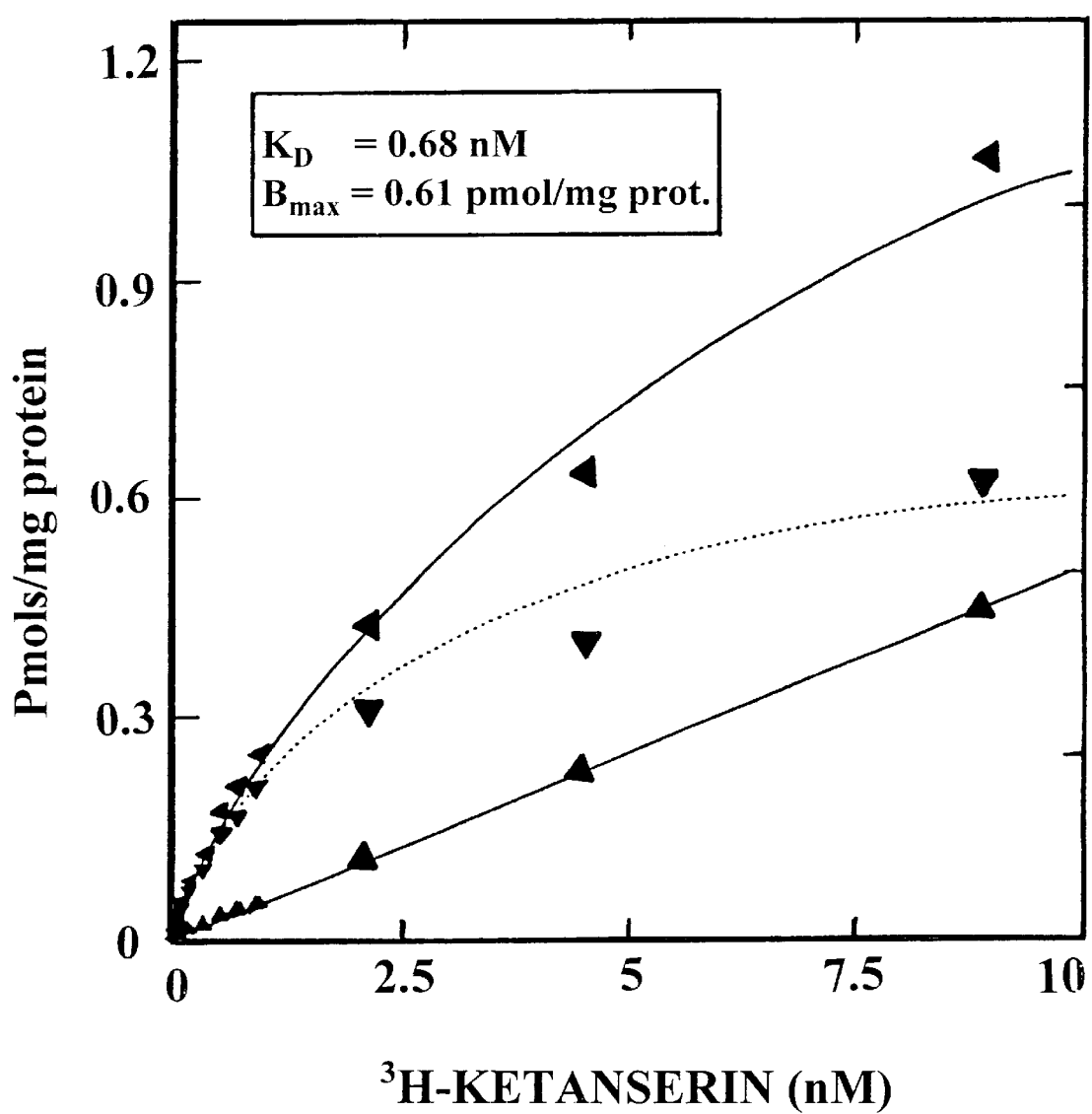

FIG. 4. Saturation Curves for the Binding of $^3$H-Ketanserin to Stably Transfected Ltk$^-$ Cells.

The lower curve represents non-specific binding as defined by $10^{-6}$M Mianserin. The middle curve is the calculated specific binding. For this experiment, $K_0$=0.678 nM; $B_{max}$=0.602 pmole/mg protein. This dissociation constant is consistent with the designation of 6B as a 5-HT$_2$ receptor.

DETAILED DESCRIPTION OF THE INVENTION

This invention proves an isolated nucleic acid molecule encoding a human 5-HT$_2$ receptor, for example a DNA molecule or a cDNA molecule.

This invention provides DNA encoding a 5-HT$_2$ receptor, for example the genomic DNA or cDNA having a coding sequence substantially the same as the coding sequence shown in FIG. 2.

This invention provides an isolated protein which is a human 5-HT$_2$ receptor. An example of such a protein has substantially the same amino acid sequence as the amino acid sequence shown in FIG. 2. A means for obtaining isolated human 5-HT$_2$ receptor is expressing DNA encoding the receptor in a suitable host, such as a bacterial, yeast, or mammalian cell, using methods well known in the art, and recovering the 5-HT$_2$ receptor after it has been expressed in such a host, again using methods well known in the art.

This invention provides vectors comprising DNA encoding a human 5-HT$_2$ receptor, and DNA and cDNA having a coding sequence substantially the same as the coding sequence shown in FIG. 2. Some examples are a plasmid, such as pUC18, or a virus, or a bacteriophage such as lambda bacteriophage.

One example of a plasmid comprising DNA having a coding sequence substantially the same as the coding sequence shown in FIG. 2 is the plasmid designated clone 6B.

This invention further provides a plasmid adapted for expression in a bacterial, yeast, or mammalian cell which comprises DNA encoding the 5-HT$_2$ receptor, or DNA or cDNA having a coding sequence substantially the same as the coding sequence shown in FIG. 2, and the regulatory elements necessary to express such DNA in the bacterial, yeast, or mammalian cell. As regards the latter, those skilled in the art will readily appreciate that numerous plasmids may be constructed utilizing existing plasmids and adapted as appropriate to contain the regulatory elements necessary to express the DNA in the mammalian cell. Numerous mammalian cells may be used including, for example, the mouse fibroblast cell NIH3T3, CHO cells, HeLa cells, etc. One example of a plasmid adapted for the expression of a cDNA molecule having a coding sequence substantially the same as the coding sequence shown in FIG. 2 is the plasmid designated pMO5-6B described more fully hereinafter and deposited with the American Type Culture Collection under ATCC Accession No. 40696.

This deposit and the other deposit discussed herein were made pursuant to, and in satisfaction of, the Budapest Treaty on the International Recognition of the Deposit of Microorganisms for the Purpose of Patent Procedure and were made with the American Type Culture Collection, 10801 University Boulevard, Manassas, Va. 20110-2209.

This invention provides expression plasmids used to transfect mammalian cells, for example Ltk$^-$ cells, comprising plasmids adapted for expression in mammalian cells which comprise DNA encoding a human 5-HT$_2$ receptor, or comprising DNA or cDNA having a coding sequence substantially the same as the coding sequence shown in FIG. 2. In one presently preferred embodiment this invention provides an Ltk$^-$ cell transfected with the plasmid designated pMO5-6B. This cell line is designated L-NGC-5HT$_2$ and is deposited under ATCC Accession No. CRL10287. DNA encoding the 5-HT$_2$ receptor may be otherwise introduced into mammalian cells, e.g., by microinjection, to obtain mammalian cells which comprise DNA, e.g., cDNA or a plasmid, encoding the 5-HT$_2$ receptor.

This invention further provides a method for determining whether a ligand, such as a known or putative drug, which is not known to be capable of binding to the 5-HT$_2$ receptor, can bind to the 5-HT$_2$ receptor. This method comprises contacting a mammalian cell expressing 5-HT$_2$ receptor the with the ligand under conditions permitting binding of ligands known to bind to the 5-HT$_2$ receptor, detecting the presence of any of the ligand bound to the 5-HT$_2$ receptor and thereby determining whether the ligand binds to the 5-HT$_2$ receptor. An example of such a mammalian cell is a mammalian cell comprising a plasmid which comprises a DNA molecule encoding a human 5-HT$_2$ receptor, or DNA or cDNA molecules having coding sequences substantially the same as the coding sequence shown in FIG. 2. Another example of such a mammalian cell is an Ltk$^-$ cell comprising a plasmid which comprises a DNA molecule encoding a human 5-HT$_2$ receptor, or DNA or cDNA molecules having coding sequences substantially the same as the coding sequence shown in FIG. 2.

This invention still further provides a method of detecting the presence of mRNA coding for the 5-HT$_2$ receptor in a cell which comprises obtaining total mRNA from the cell, using well known methods, and contacting the mRNA so obtained with the cDNA having a coding sequence substantially the same as the coding sequence encoding the 5-HT$_2$ receptor shown in FIG. 2, under hybridizing conditions, detecting the presence of mRNA hybridized to the cDNA, and thereby detecting the presence of mRNA coding for the 5-HT$_2$ receptor by the cell.

This invention also provides a DNA probe useful for detecting in a sample nucleic acid encoding the 5-HT$_2$ receptor. Such a probe comprises a nucleic acid molecule of at least about 15 nucleotides having a sequence complementary to a sequence included within the sequence shown in FIG. 2. Such a nucleic acid probe technology is well known to those skilled in the art who will readily appreciate that such probes may vary greatly in length and may be labeled with a detectable label, such as a radioisotope or fluorescent dye, to facilitate detection of the probe.

This invention provides an antibody directed to the human 5-HT$_2$ receptor. Such an antibody may be serum-derived or monoclonal and may be prepared using methods well known in the art. For example, cells such as SR3T3 cells or Ltk$^-$ cells may be used as immunogens to raise such an antibody. Alternatively, synthetic peptides may be prepared using commercially available machines and the amino acid sequence shown in FIG. 2. As a still further alternative, DNA, such as a cDNA or a fragment thereof, may be cloned and expressed and the resulting polypeptide recovered and used as an immunogen. One example of such an antibody is a monoclonal antibody directed to an epitope of the 5-HT$_2$ receptor present on the surface of a cell and having an amino acid sequence substantially the same as any part of the amino acid sequence shown in FIG. 2.

Still further this invention provides a method of detecting the presence of the 5-HT$_2$ receptor on the surface of a cell which comprises contacting the cell with a monoclonal or serum-based antibody directed to an exposed epitope on the 5-HT$_2$ receptor under conditions permitting binding of the antibody to the 5-HT$_2$ receptor, and detecting the presence of the antibody bound to the cell, and thereby the presence of the 5-HT$_2$ receptor on the surface of the cell. Such a method is useful in determining whether a given cell is defective relative to the expression of 5-HT$_2$ receptor on the surface of the cell.

Finally, this invention provides a method of screening drugs to identify drugs which specifically interact with, and bind to, the 5-HT$_2$ receptor on the surface of a cell. This method comprises contacting a mammalian cell which is expressing 5-HT$_2$ receptor with a plurality of drugs, known or putative, determining those drugs which bind to the mammalian cell, and thereby identifying drugs which specifically interact with, and bind to, the 5-HT$_2$ receptor. An example of a mammalian cell is the mammalian cell comprising a plasmid which comprises a DNA molecule encoding a human 5-HT$_2$ receptor, or DNA or cDNA molecules having coding sequences substantially the same as the coding sequence shown in FIG. 2.

Specifically this invention relates to the first isolation of a human cDNA clone encoding the 5-HT$_2$ receptor and expressing a serotonergic binding site in Ltk$^-$ cells by transfecting the cells with the construct pMO5-6B. A mammalian cell line expressing a human 5-HT$_2$ receptor at the cell surface has been constructed, as determined by pharmacologic methods, thus establishing the first well-defined, cultured cell line with which to study the human 5-HT$_2$ receptor.

The cDNA molecule of the subject invention, which encodes the human 5-HT$_2$ receptor, is useful for obtaining genomic DNA, cDNA or mRNA from human, mammalian or other animal sources, or to isolate related cDNA or genomic clones by the screening of cDNA or genomic libraries. The DNA molecule is obtained by insertion of the whole molecule or fragments thereof into suitable vectors, such as plasmids or bacteriophages, wherein it is replicated and harvested following insertion into suitable bacterial host cells, using methods well known in the art. DNA or RNA fragments derived from the isolated DNA molecule are useful as probes for 'in situ' hybridization or to locate tissues which express this gene, or for other hybridization assays for the presence of the gene or its mRNA in various biological tissues. In addition, synthesized oligonucleotides complementary to the sequence of the DNA molecule are useful as probes for the 5-$HT_2$ receptor gene, for its associated mRNA, or for the isolation or related genes by homology screening of genomic or cDNA libraries, or by the use of amplification techniques such as the Polymerase Chain Reaction.

This invention is also useful to obtain the protein, or fragments of the protein, encoded by the isolated cDNA molecule encoding the human 5-$HT_2$ receptor. Transfecting suitable hosts, such as bacterial, yeast or mammalian cells, with the DNA molecule or fragments thereof in suitable expression vectors such as the plasmid pSVL, using methods well known in the art, yields expression of the 5-$HT_2$ receptor or fragments thereof for direct uses or for experimental study.

Response systems are obtained by coupling the 5-$HT_2$ receptor encoded by the isolated cDNA molecule to an appropriate second messenger response system. These second messenger response systems include, but are not limited to, such systems as phosphoinositide hydrolysis, adenylate cyclase, guanylate cyclase or ion channels. The response system is obtained by transfection of the isolated cDNA molecule into a suitable host cell containing the desired second messenger system. Such a host system is isolated from pre-existing cell lines, or is generated by inserting appropriate components of second messenger systems into existing cell lines. Such a transfection system provides a complete response system for investigation or assay of the activity of the 5-$HT_2$ receptor encoded by the isolated cDNA molecule.

This invention is useful to determine whether a ligand, such as a known or putative drug, is capable of binding to and/or activating the 5-$HT_2$ receptor encoded by the isolated cDNA molecule. Transfection of the isolated cDNA molecule into the cell systems described above provides an assay system for the ability of ligands to bind to and/or to activate the receptor encoded by the isolated DNA molecule. Transfection systems, such as those described above, are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for competitive binding assays. Functional assays of second messenger systems or their sequelae in a transfection system act as assays for binding affinity and efficacy in the the activation of receptor function. Such a transfection system constitutes a "drug discovery system", useful for the identification of natural or synthetic compounds with potential for drug development that can be further modified or used directly as therapeutic compounds to activate or inhibit the natural functions of the 5-$HT_2$ receptor encoded by the isolated cDNA molecule. The transfection system is also useful for determining the affinity and efficacy of known drugs at the human 5-$HT_2$ receptor site.

This invention is useful to isolate the genomic DNA encoding the 5-$HT_2$ receptor so that transcriptional regulatory elements from the 5' untranslated region of the isolated gene, and other stability, processing, transcription, translation, and tissue specifically-determining regions from the 3' and 5' untranslated regions of the isolated gene, are made available for further research and application.

This invention is also useful to generate antibodies directed against the 5-$HT_2$ receptor protein encoded by the isolated cDNA molecule. Expression of the protein encoded by the isolated cDNA molecule, in transfection systems such as those described above, provides protein or fragments of protein which are further useful to generate monoclonal or polyclonal antibodies against the isolated receptor, using methods well known in the art. These antibodies are useful to detect the presence of the receptor encoded by the isolated cDNA molecule, or to inhibit the function of the receptor encoded by the isolated cDNA molecule, in living animals, in humans, or in biological tissues or fluids isolated from animals or humans.

This invention identifies an individual receptor subtype protein and tests whether pharmacological compounds interact with it for use in therapeutic treatments. Pharmacological compounds which are directed against specific receptor subtypes will provide effective new therapies with minimal side effects.

In summary, this invention identifies for the first time a human 5-$HT_2$ receptor protein, its amino acid sequence, and its human gene. The information and experimental tools provided by this discovery will be useful to generate new therapeutic agents, and new therapeutic or diagnostic assays for this new receptor protein, its associated mRNA or its associated genomic DNA.

The invention will be better understood by reference to the Experimental Details which follow, but those skilled in the art will readily appreciate that the specific experiments detailed are only illustrative of the invention as described more fully in the claims which follow thereafter.

Experimental Details

Isolation of a rat 5-$HT_{1C}$ receptor cDNA clone

The rat 5-$HT_{1C}$ gene was isolated as a prerequisite to isolating a clone for the human 5-$HT_2$ gene. This gene was obtained by isolating clones from a rat choroid plexus cDNA library specifically primed with an oligomer complementary to the 3' untranslated region of the rat 5-$HT_{1C}$ receptor. Oligomers complementary to the rat 5-$HT_{1C}$ published sequence (Julius, et al., Science 241: 558–564 (1988) were labeled with $^{32}$P-ATP and T4 Kinase (Maniatis et al, 1982). Clones showing positive hybridization to the probe were picked and inserts subcloned into the sequencing vector pUR250 (Ruther, Nucl. Acids Res 10:5765–5772 (1982)). Sequencing via the Sanger dideoxy method (Sanger, et. al., Proc. Natl. Acad. Sci. 74:5463–5467 (1977)) confirmed the isolation of a clone containing the entire coding region of the gene.

Isolation of a human 5-$HT_2$ receptor cDNA clone.

Initially, a human brain stem cDNA library provided by Stratagene (La Jolla, Calif.) was screened using a probe made from a rat 5-$HT_{1C}$ receptor gene. This gene had been subcloned into the vector pGem1 (Sma I to Eco RI; Promega-Biotec; Madison, Wis.). Sense strand RNA transcribed by Sp6 polymerase served as a template for the generation of a high specific activity cDNA which was produced by reverse transcription with AMV reverse transcriptase and random primers. The reason for using this particular method was to avoid background problems we have encountered when generating probes using other methods.

Hybridization was performed at 60° C. in a solution containing 5 X SSC (1 X SSC is 0.15 M sodium chloride, 0.015 M sodium citrate), 2 X Denhardt's (0.02% polyvinylpyrrvolidone, 0.02% Ficoll, and 0.02% bovine serum albumin), 100 mM sodium phosphate pH 8.0, 25 mM EDTA, 0.1% SDS (sodium dodecyl sulfate) and 100 μg/ml of sonicated sperm DNA. The filters were washed at 60° C. in 0.1 X SSC containing 0.1% sodium dodecyl sulfate (SDS) and exposed at −70° C. to Kodak XAR film in the presence of an intensifying screen. Lambda phage hybridizing to the probe were plaque purified and plasmid DNA (in the vector pBluescript) self-excised from the lambda vector (lambda ZAP).

One clone (Clone 15) displayed high homology to the published sequence of a rat $5-HT_2$ receptor clone (Pritchett, et al., EMBO J. 7: 4135–4140 (1988)). However, this clone did not contain the entire coding region and was therefore nonfunctional.

Isolation of a functional human $5-HT_2$ receptor cDNA clone $^{32}P$-labeled oligomers complementary to the 5' end of Clone 15 were used to probe a human temporal cortex cDNA library (Stratagene, La Jolla, Calif.). Methods for labeling and hybridization are identical to the above. Four independent clones were isolated with the probe, and one, designated 6B, was selected for further studies.

Clone 6B contained the entire coding region for a $5-HT_2$ receptor and was therefore predicted to be functional. The sequence of this clone is displayed in FIG. 2. Clone 6B was subcloned into the mammalian expression vector pMO5 to obtain the construct pMO5-6B.

DNA Sequencing

Nucleotide sequence analysis was done by the Sanger dideoxy nucleotide chain-termination method (Sanger, et al., Proc. Natl. Acad. Sci., 74: 5463–5467, 1977) on denatured double-stranded plasmid templates (Chen and Seeburg, DNA 4: 165, 1985) using Sequenase (U.S. Biochemical Corp., Cleveland, Ohio).

$^3H$-Ketanserin(64.9/mmol;DuPont-NEN, Wilmington, Del.) Binding to Transiently Transfected Cos-7 Cells:

$^3H$-Ketanserin was used as a radioligand to detect expression of the $5-HT_2$ gene in transiently transfected Cos-7 cells. Membranes were incubated in 96 well microtiter plates at 37° C. for 15' in solution containing buffer [50 mM Tris Cl, 0.5 mM EDTA, 10 mM $MgSO_4$, 0.1% ascorbate and 10 μM pargyline pH 7.6] 1–2 nM $^3H$-Ketanserin (64.9 Ci/mmol; DuPont-NEN, Wilmington, Del.), 20–40 μg/0.25 ml protein, and drugs. The total reaction volume was 0.25 ml. The reaction was terminated by filtration through GF/B filters using a Brandel Cell Harvester Model 48R (Brandel, Gaithersburg, Md.). Filters were washed 5×1 sec. with iced buffer to reduce non-specific binding. Dried filters were transferred to scintillation vials and counted by liquid scintillation spectroscopy using a Beckman LS 1701 LSC. Two and one half ml of Formula 963 (Beckman Instruments, Fullerton, Calif.) was used as cocktail. Specific binding was 95% of total binding in transiently transfected cells.

$^3H$-DOB (20.8 Ci/mmole; DuPont-NEN; Wilmington, Del.) Binding to Transiently Transfected Cos-7 Cells.

Membranes were incubated identically as described for $^3H$-Ketanserin (above). $^3H$-DOB (20.8 Ci/mmol; DuPont-NEN; Wilmington, Del.) was used as a radioligand at a final concentration of 1–2 nM. Specific binding was 70% of total binding in transiently transfected Cos-7 cells.

Saturation Studies

To determine the equilibrium dissociation constant of the $5-HT_2$ receptor, saturation analysis was performed using $^3H$-Ketanserin as a radioligand. The concentration of the $^3H$-Ketanserin covered a range between 0.25 and 20 nM. Mianserin at 1.0 μM was used to define specific binding. Incubation time was 60 minutes. All conditions were as described above. Data was analyzed by computer assisted non-linear regression (Accufit Saturation; Lundon Software; Chagrin Falls, Ohio).

Method for Binding Assays On a Stable Cell Line

Subsequent to analysis in transiently transfected cells, the $5-HT_2$ clone was expressed as a stable transfectant in mouse $Ltk^-$ cells. Further characterization was done on these cells as described above. Specific binding was 75–85% of the total binding.

Competition studies for $^3H$-Ketanserin binding were performed by adding increasing concentrations of test drug to the reaction. 10–12 different concentrations of each ligand were tested and spanned the expected $IC_{50}$ range as determined from literature values. Data were analyzed by computer-assisted analysis (Accufit Competition; Lundon Software; Chagrin Falls, Ohio).

Experimental Results

Nucleotide Sequence and Deduced Amino Acid Sequence of the Receptor Encoded by Clone 6B.

DNA sequence information obtained from clone 6B is shown in FIG. 2. An open reading frame extending from an ATG codon at position 1 to a stop codon at position 1414 can encode a protein 471 amino acids in length, having a relative molecular mass ($M_r$) of 52,542. A comparison of this protein sequence with previously characterized neurotransmitter receptors indicates that clone 6B is a new member of a family of molecules which span the lipid bilayer seven times and couple to guanine nucleotide regulatory proteins (the G protein-coupled receptor family). A variety of structural features which are invariant in this family were present in clone 6B. The greatest homology was found between clone 6B and the rat $5-HT_{1C}$ and rat $5-HT_2$ receptors. Overall, 90% sequence conservation between the rat and human $5-HT_2$ clones was observed over 471 amino acids. There is considerable divergence between rat and human protein sequences at the extracellular amino and cytoplasmic carboxy termino. Only 76% of the residues are conserved in these regions. In contrast, between these regions, which included transmembrane region domains and transmembrane loops, 98% of the residues are conserved.

Receptor Expression in Transfected Mammalian Cells

In order to confirm the functional identity of the newly isolated gene we have expressed clone 6B in cultured cell lines. A DNA fragment containing the entire coding region was subcloned into the expression vector pMO5. The resulting plasmid pMO6-6B was transiently introduced into Cos-7 cells using the DEAE-dextran protocol (Cullen, Methods in Enz. 152: 684–704, 1987).

Stable cell lines were produced by cotransfection with the plasmid containing the bacterial gene aminoglycoside phosphtransferase into $Ltk^-$ cells (American Type Culture Collection, Rockville, Md., Cell Line CCL 1, 3) using the calcium phosphatase technique (Protocol & kit obtained from Specialty Media, Inc. Lavallette, N.J.). Clones expressing aminoglycoside transferase were selected for the addition 1 mg/ml G418 (Gibco Laboratories, Grand Island, N.Y.) to the culture medium. $^3H$-Ketanserin and $^3H$-DOB binding were used to monitor $5-HT_2$ receptor gene expression in these clones. Three out of sixteen clones displayed specific binding of both $^3H$-Ketanserin and $^3H$-DOB. The remainder bound neither radioligand.

Cos-7 cells or $Ltk^-$ cells were pseudotransfected with pMO5 not containing an insert in order to asses endogenous levels of ligand binding. At 1 nM or 2 nM radioligand, no significant specific binding was detected. The background was low [100 CPM for $^3$H-Ketanserin and 20 CPM for $^3$H-DOB] for both cell lines. Therefore, Cos-7 and Ltk$^-$ cells provide useful models for transfection of a putative 5-HT$_2$ receptor. Transiently transfected Cos-7 cells bound $^3$H-Ketanserin with high affinity, and with an estimated site density of 0.95–1.6 pm/mg protein. These cells also bound $^3$H-DOB with high affinity and with a site density of 0.26–0.5 pm/mg protein. $^3$H-DOB binding constituted approximately 30% of the $^3$H-Ketanserin binding sites.

Full saturation analysis was performed on stable cell lines expressing the gene. Ltk$^-$ cells transfected with pMO5-6B bound $^3$H-Ketanserin saturably, specifically, and with high affinity. The binding constants were evaluated by computer-assisted nonlinear regression using Accufit (Lundon Software, Chagrin Falls, Ohio). The equilibrium dissociation constant was 0.678±0.13 nM and the $B_{max}$=0.602±0.07 pm/mg protein (See FIG. 4). Further characterization was accomplished by performing competition experiments for a series of drugs. Analysis of the competition data was accomplished using the computer-assisted nonlinear regression program Accucomp. Data are shown in Table 1.

TABLE 1

PROPERTIES OF 3H-KETANSERIN BINDING TO THE CLONED HUMAN 5-HT2 RECEPTOR EXPRESSED IN LTK CELLS.

| DRUG | $K_i$ (nM) HUMAN | n | $K_i$ (nM) HUMAN CORTEX | $K_i$ (nM) RAT CORTEX[2] |
|---|---|---|---|---|
| SPIPERONE | 0.22 ± .03 | 3 | 0.42[1] | 1.5 |
| 5-HT | 224.0 ± 22 | 4 | 174[2] | 79 |
| MESULERGINE | 146 ± 5 | 2 | 158[2] | 5 |
| RITANSERIN | 1.29 | 1 | 1.26[2] | 7.2 |
| CYPROHEPTADINE | 2.95 ± 0.10 | 2 | 6.3[2] | 1.8 |
| METHYSERGIDE | 2.62 ± 0.12 | 2 | 2.5[2] | 4 |
| BUTACLAMOL | 9.0 | 1 | 2.4[1] | — |
| 5-CT | 3032 | 1 | 813[2] | 19953 |

[1]Lyon, et al., Mol. Pharmacol. 31: 194–199 (1987).
[2]Hoyer, et al., Brain Res. 376: 97–107 (1986).

The high affinity of pMO5-6B transfected Cos-7 or Ltk$^-$ membranes for $^3$H-Ketanserin indicates that this clone can code for the production of 5-HT$_2$ binding site in its otherwise naive host cells.

Discussion

Applicants have cloned and characterized a cDNA molecule encoding an human 5-HT$_2$ receptor. The expression of this cDNA clone in Cos-7 cells and Ltk$^-$ cells results in the appearance of this type of receptor on the cell surface.

Binding competition studies of pMO5-6B transfected Cos-7 or Ltk$^-$ cell membranes with $^3$H-Ketanserin (Table 1) indicate that this clone is a 5-HT$_2$ receptor. Furthermore, the pharmacological profile of the cloned human receptor closely matches that of the $^3$H-Ketanserin binding to the 5-HT$_2$ receptor in human cortical membranes rather than in rat cortical membranes even though the human receptor was expressed (by transfection) in a mouse fibroblast cell line (Ltk$^-$). This species difference is particularly evident for Mesulergine (see Table 1). This data strongly suggests that the species differences in pharmacological binding properties of the human 5-HT$_2$ receptor arise from amino acid differences in this protein rather than the cellular environment in which it is translated, processed and inserted in the cell membrane. Thus, the key parameter in obtaining a human-like pharmacology of the 5-HT$_2$ receptor appears to be the human gene sequence, rather than the cell type in which it is expressed. Therefore, isolation of the human gene provides the critical tool needed for the development of heterologous expression systems which will accurately model the pharmacological properties of human brain tissue. Moreover, the fact that these transfected cell membranes bind both $^3$H-Ketanserin and $^3$H-DOB demonstrates that the reported "hallucinogen receptor" must be an affinity state of the 5-HT$_2$ receptor rather than a distinct receptor subtype. This observation provides the opportunity to use the transfected human 5-HT$_2$ receptor as a tool for the development of drugs which induce or which interfere with hallucinogenesis, caused either by disease processes or by drugs of abuse.

What is claimed is:

1. A method of obtaining a composition comprising a compound that specifically binds to a human 5-HT$_2$ receptor, said method comprising determining whether a chemical compound specifically binds to a human 5-HT$_2$ receptor expressed on the surface of a mammalian cell transfected with a vector adapted for expressing the receptor in the cell, and if the compound specifically binds to the receptor, admixing the compound with a carrier, wherein the human 5-HT$_2$ receptor comprises an amino acid sequence (a) identical to the amino acid sequence of the human 5-HT$_2$ receptor shown in FIG. 2 (SEQ ID NO: 2) or (b) identical to the amino acid sequence of the human 5-HT$_2$ receptor encoded by plasmid pM05-6B (ATCC Accession No. 40696).

2. A method of obtaining a composition comprising a compound which interacts with and specifically binds to a human 5-HT$_2$ receptor, said method comprising screening compounds to identify a compound which interacts with and specifically binds to a human 5-HT$_2$ receptor expressed on the surface of a mammalian cell transfected with a vector adapted for expressing the receptor in the cell, and if the compound interacts with and specifically binds to the receptor, admixing the compound with a carrier, wherein the human 5-HT$_2$ receptor comprises an amino acid sequence (a) identical to the amino acid sequence of the human 5-HT$_2$ receptor shown in FIG. 2 (SEQ ID NO: 2) or (b) identical to the amino acid sequence of the human 5-HT$_2$ receptor encoded by plasmid pM05-6B (ATCC Accession No. 40696).

3. A method of obtaining a composition comprising a compound which binds to and activates a human 5-HT$_2$ receptor, said method comprising determining whether a chemical compound binds to and activates a human 5-HT$_2$ receptor expressed on the surface of a mammalian cell, wherein the human 5-HT$_2$ receptor is expressed on the surface of a mammalian cell transfected with a vector adapted for expressing the receptor in the cell, and if the compound binds to and activates the receptor, admixing the compound with a carrier, wherein the human 5-HT$_2$ receptor comprises an amino acid sequence (a) identical to the amino acid sequence of the human 5-HT$_2$ receptor shown in FIG. 2 (SEQ ID NO: 2) or (b) identical to the amino acid sequence of the human 5-HT$_2$ receptor encoded by plasmid M05-6B (ATCC Accession No. 40696).

4. A method of obtaining a composition comprising a compound which binds to and inhibits activation of a human 5-HT$_2$ receptor, said method comprising determining whether a chemical compound binds to and inhibits activation of a human 5-HT$_2$ receptor expressed on the surface of a mammalian cell, wherein the human 5-HT$_2$ receptor is expressed on the surface of a mammalian cell transfected with a vector adapted for expressing the receptor in the cell, and if the compound binds to and inhibits activation of the receptor, admixing the compound with a carrier, wherein the human 5-HT$_2$ receptor comprises an amino acid sequence (a) identical to the amino acid sequence of the human 5-HT$_2$ receptor shown in FIG. 2 (SEQ ID NO: 2) or (b) identical to the amino acid sequence of the human 5-HT$_2$ receptor encoded by plasmid pM05-6B (ATCC Accession No. 40696).

5. A method of any one of claims 1, 2, 3, or 4, wherein the composition is a pharmaceutical composition and the carrier is a pharmaceutically acceptable carrier.

* * * * *

SEQUENCE LISTING

```
<160> NUMBER OF SEQ ID NOS: 4

<210> SEQ ID NO 1
<211> LENGTH: 1483
<212> TYPE: DNA
<213> ORGANISM: Homo sapiens
<220> FEATURE:
<221> NAME/KEY: CDS
<222> LOCATION: (1)..(1440)

<400> SEQUENCE: 1 atg gat att ctt tgt gaa gaa aat act tct ttg agc tca act acg aac        48
Met Asp Ile Leu Cys Glu Glu Asn Thr Ser Leu Ser Ser Thr Thr Asn
  1               5                  10                  15 tcc cta atg caa tta aat gat gac acc agg ctc tac agt aat gac ttt        96
Ser Leu Met Gln Leu Asn Asp Asp Thr Arg Leu Tyr Ser Asn Asp Phe
             20                  25                  30 aac tcc gga gaa gct aac act tct gat gca ttt aac tgg aca gtc gac       144
Asn Ser Gly Glu Ala Asn Thr Ser Asp Ala Phe Asn Trp Thr Val Asp
         35                  40                  45
```

```
tct gaa aat cga acc aac ctt tcc tgt gaa ggg tgc ctc tca ccg tcg      192
Ser Glu Asn Arg Thr Asn Leu Ser Cys Glu Gly Cys Leu Ser Pro Ser
    50              55                  60 tgt ctc tcc tta ctt cat ctc cag gaa aaa aac tgg tct gct tta ctg      240
Cys Leu Ser Leu Leu His Leu Gln Glu Lys Asn Trp Ser Ala Leu Leu
65              70                  75                  80 aca gcc gta gtg att att cta act att gct gga aac ata ctc gtc atc      288
Thr Ala Val Val Ile Ile Leu Thr Ile Ala Gly Asn Ile Leu Val Ile
                85                  90                  95 atg gca gtg tcc cta gag aaa aag ctg cag aat gcc acc aac tat ttc      336
Met Ala Val Ser Leu Glu Lys Lys Leu Gln Asn Ala Thr Asn Tyr Phe
            100                 105                 110 ctg atg tca ctt gcc ata gct gat atg ctg ctg ggt ttc ctt gtc atg      384
Leu Met Ser Leu Ala Ile Ala Asp Met Leu Leu Gly Phe Leu Val Met
        115                 120                 125 ccc gtg tcc atg tta acc atc ctg tat ggg tac cgg tgg cct ctg ccg      432
Pro Val Ser Met Leu Thr Ile Leu Tyr Gly Tyr Arg Trp Pro Leu Pro
    130                 135                 140 agc aag ctt tgt gca gtc tgg att tac ctg gac gtg ctc ttc tcc acg      480
Ser Lys Leu Cys Ala Val Trp Ile Tyr Leu Asp Val Leu Phe Ser Thr
145                 150                 155                 160 gcc tcc atc atg cac ctc tgc gcc atc tcg ctg gac cgc tac gtc gcc      528
Ala Ser Ile Met His Leu Cys Ala Ile Ser Leu Asp Arg Tyr Val Ala
                165                 170                 175 atc cag aat ccc atc cac cac agc cgc ttc aac tcc aga act aag gca      576
Ile Gln Asn Pro Ile His His Ser Arg Phe Asn Ser Arg Thr Lys Ala
            180                 185                 190 ttt ctg aaa atc att gct gtt tgg acc ata tca gta ggt ata tcc atg      624
Phe Leu Lys Ile Ile Ala Val Trp Thr Ile Ser Val Gly Ile Ser Met
        195                 200                 205 cca ata cca gtc ttt ggg cta cag gac gat tcg aag gtc ttt aag gag      672
Pro Ile Pro Val Phe Gly Leu Gln Asp Asp Ser Lys Val Phe Lys Glu
    210                 215                 220 ggg agt tgc tta ctt gcc gat gat aac ttt gtc ctg atc ggc tct ttt      720
Gly Ser Cys Leu Leu Ala Asp Asp Asn Phe Val Leu Ile Gly Ser Phe
225                 230                 235                 240 gtg tca ttt ttc att ccc tta acc atc atg gtg atc acc tac ttt cta      768
Val Ser Phe Phe Ile Pro Leu Thr Ile Met Val Ile Thr Tyr Phe Leu
                245                 250                 255 act atc aag tca ctc cag aaa gaa gct act ttg tgt gta agt gat ctt      816
Thr Ile Lys Ser Leu Gln Lys Glu Ala Thr Leu Cys Val Ser Asp Leu
            260                 265                 270 ggc aca cgg gcc aaa tta gct tct ttc agc ttc ctc cct cag agt tct      864
Gly Thr Arg Ala Lys Leu Ala Ser Phe Ser Phe Leu Pro Gln Ser Ser
        275                 280                 285 ttg tct tca gaa aag ctc ttc cag cgg tcg atc cat agg gag cca ggg      912
Leu Ser Ser Glu Lys Leu Phe Gln Arg Ser Ile His Arg Glu Pro Gly
    290                 295                 300 tcc tac aca ggc agg agg act atg cag tcc atc agc aat gag caa aag      960
Ser Tyr Thr Gly Arg Arg Thr Met Gln Ser Ile Ser Asn Glu Gln Lys
305                 310                 315                 320 gca tgc aag gtg ctg ggc atc gtc ttc ttc ctg ttt gtg gtg atg tgg     1008
Ala Cys Lys Val Leu Gly Ile Val Phe Phe Leu Phe Val Val Met Trp
                325                 330                 335 tgc cct ttc ttc atc aca aac atc atg gcc gtc atc tgc aaa gag tcc     1056
Cys Pro Phe Phe Ile Thr Asn Ile Met Ala Val Ile Cys Lys Glu Ser
            340                 345                 350 tgc aat gag gat gtc att ggg gcc ctg ctc aat gtg ttt gtt tgg atc     1104
Cys Asn Glu Asp Val Ile Gly Ala Leu Leu Asn Val Phe Val Trp Ile
```

-continued

```
           355                 360                 365
ggt tat ctc tct tca gca gtc aac cca cta gtc tac aca ctg ttc aac      1152
Gly Tyr Leu Ser Ser Ala Val Asn Pro Leu Val Tyr Thr Leu Phe Asn
    370                 375                 380 aag acc tat agg tca gcc ttt tca cgg tat att cag tgt cag tac aag      1200
Lys Thr Tyr Arg Ser Ala Phe Ser Arg Tyr Ile Gln Cys Gln Tyr Lys
385                 390                 395                 400 gaa aac aaa aaa cca ttg cag tta att tta gtg aac aca ata ccg gct      1248
Glu Asn Lys Lys Pro Leu Gln Leu Ile Leu Val Asn Thr Ile Pro Ala
            405                 410                 415 ttg gcc tac aag tct agc caa ctt caa atg gga caa aaa aag aat tca      1296
Leu Ala Tyr Lys Ser Ser Gln Leu Gln Met Gly Gln Lys Lys Asn Ser
                420                 425                 430 aag caa gat gcc aag aca aca gat aat gac tgc tca atg gtt gct cta      1344
Lys Gln Asp Ala Lys Thr Thr Asp Asn Asp Cys Ser Met Val Ala Leu
            435                 440                 445 gga aag cag cat tct gaa gag gct tct aaa gac aat agc gac gga gtg      1392
Gly Lys Gln His Ser Glu Glu Ala Ser Lys Asp Asn Ser Asp Gly Val
        450                 455                 460 aat gaa aag gtg agc tgt gtg tga tag gct agt tgc cgt ggc aac tgt      1440
Asn Glu Lys Val Ser Cys Val         Ala Ser Cys Arg Gly Asn Cys
465                 470                 475                 480 ggaaggcaca ctgagcaagt tttcacctat ctggtttttt ttg                      1483
```

<210> SEQ ID NO 2
<211> LENGTH: 471
<212> TYPE: PRT
<213> ORGANISM: Homo sapiens

<400> SEQUENCE: 2

```
Met Asp Ile Leu Cys Glu Glu Asn Thr Ser Leu Ser Ser Thr Thr Asn
  1               5                  10                  15

Ser Leu Met Gln Leu Asn Asp Asp Thr Arg Leu Tyr Ser Asn Asp Phe
                 20                  25                  30

Asn Ser Gly Glu Ala Asn Thr Ser Asp Ala Phe Asn Trp Thr Val Asp
             35                  40                  45

Ser Glu Asn Arg Thr Asn Leu Ser Cys Glu Gly Cys Leu Ser Pro Ser
         50                  55                  60

Cys Leu Ser Leu Leu His Leu Gln Glu Lys Asn Trp Ser Ala Leu Leu
 65                  70                  75                  80

Thr Ala Val Val Ile Ile Leu Thr Ile Ala Gly Asn Ile Leu Val Ile
                     85                  90                  95

Met Ala Val Ser Leu Glu Lys Lys Leu Gln Asn Ala Thr Asn Tyr Phe
                100                 105                 110

Leu Met Ser Leu Ala Ile Ala Asp Met Leu Leu Gly Phe Leu Val Met
            115                 120                 125

Pro Val Ser Met Leu Thr Ile Leu Tyr Gly Tyr Arg Trp Pro Leu Pro
130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205
```

-continued

```
Pro Ile Pro Val Phe Gly Leu Gln Asp Asp Ser Lys Val Phe Lys Glu
    210                 215                 220
Gly Ser Cys Leu Leu Ala Asp Asp Asn Phe Val Leu Ile Gly Ser Phe
225                 230                 235                 240
Val Ser Phe Phe Ile Pro Leu Thr Ile Met Val Ile Thr Tyr Phe Leu
                245                 250                 255
Thr Ile Lys Ser Leu Gln Lys Glu Ala Thr Leu Cys Val Ser Asp Leu
            260                 265                 270
Gly Thr Arg Ala Lys Leu Ala Ser Phe Ser Phe Leu Pro Gln Ser Ser
        275                 280                 285
Leu Ser Ser Glu Lys Leu Phe Gln Arg Ser Ile His Arg Glu Pro Gly
    290                 295                 300
Ser Tyr Thr Gly Arg Arg Thr Met Gln Ser Ile Ser Asn Glu Gln Lys
305                 310                 315                 320
Ala Cys Lys Val Leu Gly Ile Val Phe Phe Leu Phe Val Val Met Trp
                325                 330                 335
Cys Pro Phe Phe Ile Thr Asn Ile Met Ala Val Ile Cys Lys Glu Ser
            340                 345                 350
Cys Asn Glu Asp Val Ile Gly Ala Leu Leu Asn Val Phe Val Trp Ile
        355                 360                 365
Gly Tyr Leu Ser Ser Ala Val Asn Pro Leu Val Tyr Thr Leu Phe Asn
    370                 375                 380
Lys Thr Tyr Arg Ser Ala Phe Ser Arg Tyr Ile Gln Cys Gln Tyr Lys
385                 390                 395                 400
Glu Asn Lys Lys Pro Leu Gln Leu Ile Leu Val Asn Thr Ile Pro Ala
                405                 410                 415
Leu Ala Tyr Lys Ser Ser Gln Leu Gln Met Gly Gln Lys Lys Asn Ser
            420                 425                 430
Lys Gln Asp Ala Lys Thr Thr Asp Asn Asp Cys Ser Met Val Ala Leu
        435                 440                 445
Gly Lys Gln His Ser Glu Glu Ala Ser Lys Asp Asn Ser Asp Gly Val
    450                 455                 460
Asn Glu Lys Val Ser Cys Val
465                 470
```

<210> SEQ ID NO 3
<211> LENGTH: 7
<212> TYPE: PRT
<213> ORGANISM: Homo sapiens

<400> SEQUENCE: 3

```
Ala Ser Cys Arg Gly Asn Cys
  1               5
```

<210> SEQ ID NO 4
<211> LENGTH: 471
<212> TYPE: PRT
<213> ORGANISM: Rattus norvegicus

<400> SEQUENCE: 4

```
Met Glu Ile Leu Cys Glu Asp Met Ile Ser Leu Ser Ile Pro Met
  1               5                  10                  15
Ser Leu Met Asp Leu Gly Asp Gly Pro Ala Leu Val His Asn Asp Phe
                 20                  25                  30
Asn Ser Arg Asp Ala Asn Thr Ser Glu Ala Ser Asn Trp Thr Ile Asp
             35                  40                  45
```

-continued

```
Ala Glu Asn Arg Thr Asn Leu Ser Cys Glu Gly Tyr Leu Pro Pro Thr
     50                  55                  60

Cys Leu Ser Ile Leu His Leu Gln Glu Lys Asn Trp Ser Ala Leu Leu
 65                  70                  75                  80

Thr Thr Val Val Ile Ile Leu Thr Ile Ala Gly Asn Ile Leu Val Ile
                 85                  90                  95

Met Ala Val Ser Leu Glu Lys Lys Leu Gln Asn Ala Thr Asn Tyr Phe
                100                 105                 110

Leu Met Ser Leu Ala Ile Ala Asp Met Leu Leu Gly Phe Leu Val Met
            115                 120                 125

Pro Val Ser Met Leu Thr Ile Leu Tyr Gly Tyr Arg Trp Pro Leu Pro
    130                 135                 140

Ser Lys Leu Cys Ala Ile Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ala Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Leu
            260                 265                 270

Ser Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
    290                 295                 300

Ser Tyr Ala Gly Arg Arg Thr Met Gln Ser Ile Ser Asn Glu Gln Lys
305                 310                 315                 320

Ala Cys Lys Val Leu Gly Ile Val Phe Phe Leu Phe Val Val Met Trp
                325                 330                 335

Cys Pro Phe Phe Ile Thr Asn Ile Met Ala Val Ile Cys Lys Glu Ser
            340                 345                 350

Cys Asn Glu Asn Val Ile Gly Ala Leu Leu Asn Val Phe Val Trp Ile
        355                 360                 365

Gly Tyr Leu Ser Ser Ala Val Asn Pro Leu Val Tyr Thr Leu Phe Asn
    370                 375                 380

Lys Thr Tyr Arg Ser Ala Phe Ser Arg Tyr Ile Gln Cys Gln Tyr Lys
385                 390                 395                 400

Glu Asn Arg Lys Pro Leu Gln Leu Ile Leu Val Asn Thr Ile Pro Ala
                405                 410                 415

Leu Ala Tyr Lys Ser Ser Gln Leu Gln Val Gly Gln Lys Lys Asn Ser
            420                 425                 430

Gln Glu Asp Ala Glu Gln Thr Val Asp Asp Cys Ser Met Val Thr Leu
        435                 440                 445
```

-continued

```
Gly Lys Gln Gln Ser Glu Glu Asn Cys Thr Asp Asn Ile Glu Thr Val
        450                 455                 460

Asn Glu Lys Val Ser Cys Val
465                 470
```